(12) United States Patent
Gale et al.

(10) Patent No.: US 8,470,014 B2
(45) Date of Patent: Jun. 25, 2013

(54) STENT-CATHETER ASSEMBLY WITH A RELEASABLE CONNECTION FOR STENT RETENTION

(75) Inventors: David C. Gale, Sunnyvale, CA (US); Klaus Kleine, Los Gatos, CA (US); Anthony Abbate, Santa Clara, CA (US); Svava M. Atladottir, San Francisco, CA (US); Bin Huang, Shoreview, MN (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 849 days.

(21) Appl. No.: 11/893,316

(22) Filed: Aug. 14, 2007

(65) Prior Publication Data

US 2008/0033526 A1 Feb. 7, 2008

Related U.S. Application Data

(62) Division of application No. 10/927,601, filed on Aug. 25, 2004.

(51) Int. Cl.
*A61F 2/06* (2006.01)

(52) U.S. Cl.
USPC .......................................................... 623/1.11

(58) Field of Classification Search
USPC ................................ 623/1.11–1.12
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

U.S. Appl. No. 10/317,435, filed Dec. 11, 2002, Hossainy et al.
U.S. Appl. No. 10/879,328, filed Jun. 28, 2004, Gale et al.
U.S. Appl. No. 10/927,601, filed Aug. 25, 2004, Gale et al.
U.S. Appl. No. 11/215,713, filed Aug. 29, 2005, Limon et al.
Anonymous, *Bioabsorbable stent mounted on a catheter having optical coherence tomography capabilities*, Research Disclosure, Sep. 2004, pp. 1159-1162.

(Continued)

*Primary Examiner* — Gregory Anderson
(74) *Attorney, Agent, or Firm* — Squire Sanders (US) LLP

(57) ABSTRACT

Medical assemblies with a releasable connection and methods of constructing such medical assemblies are disclosed. The medical assemblies generally comprise a stent, a catheter assembly having catheter body a balloon, and a releasable connection between the stent and the catheter assembly that releases the stent from the catheter assembly in response to enlargement of the balloon or when the balloon has been enlarged to an expanded configuration.

24 Claims, 4 Drawing Sheets

U.S. PATENT DOCUMENTS

| | | |
|---|---|---|
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,785 A * | 2/1994 | Shapland et al. ............... 604/21 |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,222 A | 1/1997 | Susawa et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,522 A * | 9/1997 | Flomenblit et al. ........... 606/198 |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,800,526 A | 9/1998 | Anderson et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohtuki et al. |
| 5,855,618 A | 1/1999 | Patnaik et al. |
| 5,858,746 A | 1/1999 | Hubbell et al. |
| 5,865,801 A * | 2/1999 | Houser ................... 604/103.07 |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,961,536 A * | 10/1999 | Mickley et al. ............... 606/194 |
| 5,965,720 A | 10/1999 | Gryaznov et al. |
| 5,971,954 A | 10/1999 | Conway et al. |
| 5,976,181 A * | 11/1999 | Whelan et al. ............... 623/1.12 |
| 5,976,182 A | 11/1999 | Cox |

| Patent No. | Date | Inventor |
|---|---|---|
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,007,545 A * | 12/1999 | Venturelli .............. 606/108 |
| 6,010,445 A | 1/2000 | Armini et al. |
| 6,015,541 A | 1/2000 | Greff et al. |
| 6,033,436 A | 3/2000 | Steinke et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 B1 | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,013 B1 | 2/2001 | Stoltze et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,134 B1 | 6/2001 | Alt et al. |
| 6,251,135 B1 | 6/2001 | Stinson et al. |
| 6,251,142 B1 | 6/2001 | Bernacca et al. |
| 6,264,683 B1 * | 7/2001 | Stack et al. .............. 623/1.11 |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,506,202 B1 * | 1/2003 | Dutta et al. .............. 606/194 |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,562,067 B2 | 5/2003 | Mathis |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,599,314 B2 | 7/2003 | Mathis |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,682,553 B1 | 1/2004 | Webler, Jr. |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,008,446 B1 * | 3/2006 | Amis et al. .............. 623/1.21 |
| 7,235,093 B2 * | 6/2007 | Gregorich .............. 623/1.11 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0068966 A1 | 6/2002 | Holman et al. |
| 2002/0111590 A1 | 8/2002 | Davila et al. |
| 2002/0111671 A1 | 8/2002 | Stenzel |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2002/0188347 A1 | 12/2002 | Mathis |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0163140 A1 | 8/2003 | Stoltze et al. |
| 2003/0171053 A1 | 9/2003 | Sanders |
| 2003/0187495 A1 | 10/2003 | Cully et al. |
| 2003/0201581 A1 * | 10/2003 | Weber et al. .............. 264/444 |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093058 A1 * | 5/2004 | Cottone et al. .............. 623/1.11 |

| | | | |
|---|---|---|---|
| 2004/0093077 | A1 | 5/2004 | White et al. |
| 2004/0098095 | A1 | 5/2004 | Burnside et al. |
| 2004/0111149 | A1 | 6/2004 | Stinson |
| 2004/0127970 | A1 | 7/2004 | Saunders et al. |
| 2004/0143317 | A1 | 7/2004 | Stinson et al. |
| 2004/0167610 | A1 | 8/2004 | Fleming, III |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| JP | 05-103830 | 4/1993 |
| JP | 2004-510492 | 4/2004 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/28320 | 4/2002 |
| WO | WO 2004/023985 | 3/2004 |

OTHER PUBLICATIONS

Ansari, *Tubal Reanastomosis Using Absorbable Stent*, International Journal of Fertility, vol. 23, No. 4, pp. 242-243 (1978).
Ansari, *End-to-end tubal anastomosis using an absorbable stent*, Fertility and Sterility, vol. 32(2), pp. 197-201 (Aug. 1979).
Bull, *Parylene Coating for Medical Applications*, Medical Product Manufacturing News 1 pg. (Mar. 1993).
Casper et al., *Fiber-Reinforced Absorbable Composite for Orthopedic Surgery*, Polymeric Materials Science and Engineering, 53: pp. 497-501 (1985).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Feng-Chun et al., *Assessment of Tissue Blood Flow Following Small Artery Welding with an Intraluminal Dissolvable Stent*, Microsurgery, vol. 19(3), pp. 148-152 (1999).
Hahn et al., *Glow Discharge Polymers as Coatings for Implanted Devices*, ISA, pp. 109-111 (1981).
Hahn et al., *Biocompatibility of Glow-Discharge-Polymerized Films and Vacuum-Deposited Parylene*, J Applied Polymer Sci, 38, pp. 55-64 (1984).
Kelley et al., *Totally Resorbable High-Strength Composite Material*, Advances in Biomedical Polymers, 35, pp. 75-85 (1987).
Kubies et al., *Microdomain Structure in polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents 16 pgs. (1999).
Mauduit et al., *Hydrolytic degradation of films prepared from blends of high and low molecular weight poly(DL-lactic acid)s*, J. Biomed. Mater. Res. v. 30, pp. 201-207 (1996).
Martin et al., *Enhancing the biological activity of immobilized osteopontin using a type-1 collagen affinity coating*, J. Biomed. Mater Res 70A, pp. 10-19 (2004).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioresorbable implants—practical considerations*, Bone v. 19, No. 1, Supplement Jul. 1996: 109S-119S.
Pietrzak et al., *Bioabsorbable Fixation Devices: Status for the Craniomaxillofacial Surgeon*, J. Craniofaxial Surg. 2, pp. 92-96 (1997).
von Recum et al., *Degradation of polydispersed poly(L-lactic acid) to modulate lactic acid release*, Biomaterials 16, pp. 441-445 (1995).
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-l-Lactic Acid Coronary Stents in Humans*, Circulation, pp. 399-404 (2000).
Tsui et al., *Biodegradable Polymeric Stents*, Current Interventional Cardiology Reports 3, pp. 10-17 (2001).
Völkel et al., *Targeting of immunoliposomes to endothelial cells using a single -chain Fv fragment directed against human endoglin (CD105)*, Biochemica et Biophysica Acta 1663, pp. 158-166 (2004).
Yau et al. Modern Size-Exclusion Liquid Chromatography, Wiley-Interscience Publication, (1979).
International Search Report for PCT/US2005/029646 filed Aug. 18, 2005, mailed Dec. 19, 2005, 5 pgs.
U.S. Appl. No. 10/879,328, filed Jun. 28, 2004, Kleine et al.
Translation of Notification of Reasons for Refusal issued by JPO for Appl. 2007-529991, mailed Jan. 11, 2011, 6 pgs.

\* cited by examiner

STENT-CATHETER ASSEMBLY WITH A RELEASABLE CONNECTION FOR STENT RETENTION

CROSS REFERENCE TO RELATED APPLICATION

This is a divisional application of U.S. Ser. No. 10/927,601, which was filed on Aug. 25, 2004, which is incorporated herein by reference.

BACKGROUND

1. Field of the Invention

This invention relates to a medical assembly. More particularly, this invention relates to a stent-catheter assembly with a releasable connection that enhances stent retention during delivery of the stent and methods of constructing such an assembly.

2. Description of the State of the Art

A stent is a device that holds tissue in place and is often used to support tissues while healing takes place. A stent can keep "tube-shaped" structures such as, for example, blood vessels, open after surgery. Stents may also be used, for example, in creating an arterio-venous fistula in a hemodialysis patient, reattaching intestines after a temporary colostomy, and keeping a ureter open after surgical removal of a blockage in the ureter. Typically, stents can be compressed to a reduced diameter, inserted through small lumens with catheters and expanded to a larger diameter when positioned at a desired location. Examples of stents in the patent literature include U.S. Pat. Nos. 4,733,665, 4,800,882, and 4,886,062.

In the early 1990s, physicians began using stents to improve angioplasty procedures. An intraluminal coronary artery stent can be a small, self-expanding or expandable, stainless steel mesh tube that is placed within a coronary artery to keep a grafted vessel open during a coronary artery bypass graft surgery or after balloon angioplasty to prevent restenosis of the vessel.

In a typical percutaneous transluminal coronary angioplasty (PTCA) procedure, a guiding catheter is inserted percutaneously through a brachial or femoral artery and advanced through the vasculature until the distal end of the guiding catheter is in a desired position within a lumen of a coronary artery. A guidewire and a dilatation catheter having a balloon on the distal end are introduced through the guiding catheter. The guidewire is advanced into the patient's coronary vasculature, and the dilatation catheter is advanced over the guide wire until the balloon is properly positioned in the lumen of the artery across an arterial lesion such as, for example, a lesion of atherosclerotic plaque or a calcified lesion.

The balloon is inflated to a predetermined size with a radiopaque liquid at a relatively high pressure to radially compress the lesion and remodel the lumen of the artery. The balloon is deflated, the dilatation catheter is withdrawn from the patient, and the blood flow is resumed through the dilated artery. To avoid restenosis, an intravascular stent can be implanted to maintain vascular patency. The stent is typically transported through the patient's vasculature on the balloon portion of a catheter.

A problem with current stent-catheter assemblies is that the stent may become detached during the process of positioning the stent in a patient's vasculature. The combination of the stent and dilatation catheter must have a small, delivery diameter and, the stent must be firmly attached to the catheter to avoid detachment of the stent before it is properly positioned in the lumen of the vasculature.

Crimping is currently used to attach stents to dilatation catheters and may fail. This failure is problematic, since loss of the stent during positioning can result in medical complications. A lost stent is, in effect, an embolus that can create a thrombosis and require surgical intervention. One approach to solving the problem of lost stents has been to attach stents to balloons with a pressure sensitive adhesive, which simply anchors the stent on the balloon. Unfortunately, pressure sensitive adhesives have created additional problems. One problem is that the stent may be damaged or displaced upon deflation of the balloon. Another problem is that residual adhesive may be physically moved to the stent's inner surface upon deflation of the balloon, where the adhesive can affect the movement of other catheters and guidewires through the stent, as well as the biocompatibility of the stent.

Another approach to solving the problem of lost stents has been to attach stents to balloons with a photodegradable adhesive. The photodegradable adhesive is degraded by directing light to the adhesive after proper positioning and delivery of the stent. Unfortunately, photodegradable adhesives require including optical fiber in the stent-catheter assembly, which increases both the cost and physical size of the assembly—two factors that are unappealing to a cardiovascular surgeon.

Accordingly, one of skill in the art would benefit from a stent-catheter assembly having a connection that retains the stent for proper delivery and placement, releases the stent without damaging or displacing the stent from its desired location, does not reduce biocompatibility, and is appealing to one of skill in the art due to any combination of a variety of factors including, but not limited to, ease of use, biocompatibility, therapeutic and prophylactic benefit to the patient, and cost.

SUMMARY

Stent-catheter assemblies and methods of constructing and using these assemblies are provided. One embodiment provides a medical assembly comprising a stent, a catheter comprising a balloon having the stent positioned on the balloon, the balloon having a deflated configuration and capable of being enlarged to an expanded configuration, and a releasable connection between the stent and the balloon that releases the stent from the balloon in response to enlargement of the balloon or when the balloon has been enlarged to an expanded configuration.

Another embodiment provides a medical assembly comprising a biodegradable stent configured to remain in a lumen of a mammal for a temporary duration of time; a catheter comprising an expandable member having the stent positioned on the expandable member, the member capable of being expanded from a collapsed profile to an expanded profile; and a means for releasably connecting the stent to the member such that in response to the expansion of the member, the biodegradable stent is detached from the member.

Another embodiment provides a medical assembly comprising a stent; a catheter assembly comprising a catheter body and a balloon having the stent positioned on the balloon, the balloon having a deflated configuration and capable of being enlarged to an expanded configuration; and a releasable connection between the stent and the catheter body, wherein the releasable connection is formed in a region outside of the balloon, and the releasable connection releases the stent from the catheter body in response to enlargement of the balloon or when the balloon has been enlarged to an expanded configuration.

Another embodiment provides a method for constructing a medical assembly comprising placing a stent over a balloon of a catheter assembly and forming a releasable connection between the stent and the catheter assembly such that in response to the enlargement of the balloon or when the balloon has been enlarged to an expanded configuration, the stent is detached from the catheter assembly.

DETAILED DESCRIPTION

As discussed in more detail below, the invention generally comprises a medical assembly and a method of constructing and using the assembly. The medical assembly includes a catheter assembly having a balloon, a stent, an adhesive, and a characteristic that the stent can be delivered and detached upon inflation of the balloon without losing the stent, damaging the stent, or displacing the stent from its desired location.

Figure 1A:
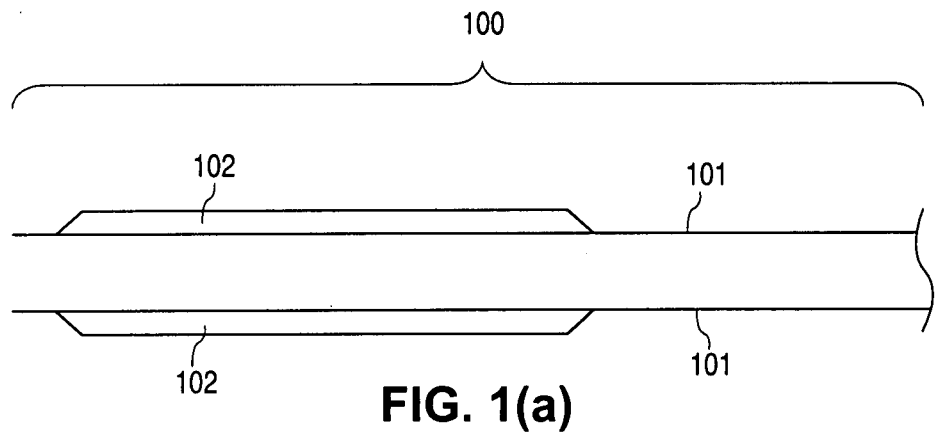
FIGS. 1a and 1b illustrate a method of constructing a medical assembly with a releasable connection formed between a stent and a catheter according to embodiments of the present invention.
Figure 1B:
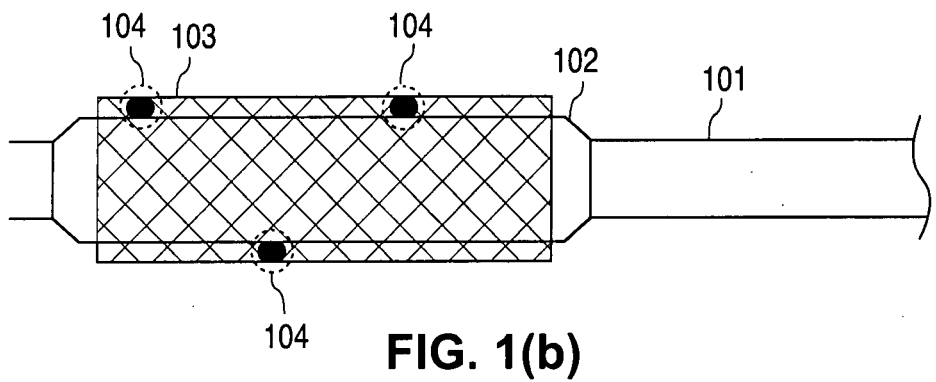

FIGS. 1a and 1b illustrate a method of constructing a medical assembly with a releasable connection formed between a stent and a catheter according to embodiments of the present invention. The medical assembly has a catheter assembly 100 having a catheter body 101 and a balloon 102; a stent 103; and a releasable connection 104. The catheter assembly 100 having a catheter body 101 and a balloon 102 is shown in FIG. 1a. In FIG. 1b, the stent 103 is placed around the balloon 102 and a releasable connection 104 is formed between the balloon 102 and the stent 103 to complete construction of the medical assembly. In this embodiment, the stent 103 has a reduced diameter that can be expanded upon dilation of the balloon 102.

It should be appreciated that stent 103 can have a range of diameters from below a reduced diameter to above an expanded diameter during formation of a stent-catheter assembly. A completed stent-catheter assembly, however, should have a stent 103 with a reduced diameter connected to the catheter assembly 100 for purposes of properly delivering the stent 103 in a lumen within a mammal without loss, damage or displacement of the stent 103. A stent 103 with a reduced diameter can be formed prior to placing the stent 103 around the balloon 102 or, a stent 103 with an expanded diameter can be placed over the balloon 102 and then crimped onto the balloon 102 using any crimping mechanism known to one of skill in the art.

The catheter body 101 and the balloon 102 can be made from any materials and have any dimensions known to be useful to one of skill in the art. Examples of materials used to make the catheter body 101 include, but are not limited to, polyvinyl chloride (PVC), polyethylene, silicone rubber, polyurethane, and any analogs, homologues, congeners, derivatives, salts, copolymers, and mixtures thereof. Examples of materials used to make the balloon 102 include, but are not limited to, latex, polyamide, nylon, polyethylene, low-density polyethylene (LDPE), Duralyn® (Cordis Corp.), Duramax® (Cordis Corp.), and any analogs, homologues, congeners, derivatives, salts, copolymers, and mixtures thereof.

The stent 103 can resemble a tube-like body that is used to open a lumen within an organ in a mammal, maintain lumen patency, or reduce the likelihood that the lumen will narrow again. Examples of such organs include, but are not limited to, vascular organs such as, for example, coronary arteries or hepatic veins; renal organs such as, for example, urethras and ureters; biliary organs such as, for example, biliary ducts; pulmonary organs such as, for example, tracheas, bronchi and bronchioles; and gastrointestinal organs such as, for example, esophagi and colons, to name a few.

The stent 103 can be composed of any materials and have any dimensions known to be useful to one of skill in the art. In some embodiments, the stents include, but are not limited to, tubular stents, self-expanding stents, coil stents, ring stents, multi-design stents, and the like. In other embodiments, the stents are metallic; low-ferromagnetic; non-ferromagnetic; biostable polymeric; biodegradable polymeric or biodegradable metallic. In some embodiments, the stents are coated such as, for example, with a polymer containing a drug. The polymer can be exclusively on the outer surface, exclusively on the inner surface, or on both the outer surface and the inner surface of the stent.

Since the stent 103 can be placed in a variety of organs within a mammal, it can have a variety of dimensions. In some embodiments, the diameter of the stent 103 can range from about 0.025 mm to about 50 mm, from about 0.05 mm to about 25 mm, from about 0.1 mm to about 20 mm, from about 0.25 mm to about 15 mm, from about 0.50 mm to about 10 mm, from about 1.0 mm to about 5 mm, or any range therein. In other embodiments, the diameter of the stent 103 can range from about 0.05 mm to about 2.5 mm, from about 0.10 mm to about 2.0 mm, from about 0.25 mm to about 1.5 mm, from about 0.50 mm to about 1.0 mm, or any range therein. In other embodiments, the diameter of the stent 103 can range from about 10 mm to about 25 mm, from about 12 mm to about 22 mm, from about 15 mm to about 20 mm, or any range therein. In some embodiments, the length of the stent 103 can range from about 0.1 mm to about 100 mm, from about 0.5 mm to about 75 mm, from about 1.0 mm to about 50 mm, from about 1.5 mm to about 40 mm, from about 2.0 mm to about 30 mm, or any range therein. The diameter of the catheter body 101 varies in correlation with the diameter of the stent 103. The catheter body 101 can be any length known to one of skill in the art to be useful in the practice of the present invention.

The stents 103 can be composed of a metal, an alloy, a polymer, or a combination thereof. Examples of materials used to form stents include, but are not limited to, ELASTINITE® (Guidant Corp.), NITINOL (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies), and combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum.

The stents 103 of the present invention can be formed using bioabsorbable polymers or biostable polymers. For the purposes of the present invention, a polymer or coating is "bioabsorbable" or "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is "degradable or erodable" when it can be gradually broken-down, resorbed, absorbed and eliminated by, for example, hydrolysis, enzymolysis, metabolic processes, bulk or surface erosion, and the like within a mammal. It should be appreciated that traces or residue of polymer may remain following biodegradation. The terms "bioabsorbable," "biodegradable," and "bioerodable" are used interchangeably in this application. A "biostable" polymer is a polymer that is not bioabsorbable.

In general, the polymers used in the present invention may be hydrophobic, hydrophilic, amphiphilic, biodegradable, or a combination thereof. Examples of hydrophobic polymers include, but are not limited to, poly(ester amide), polystyrene-polyisobutylene-polystyrene block copolymer (SIS), polystyrene, polyisobutylene, polycaprolactone (PCL), poly (L-lactide), poly(D,L-lactide), polylactic acid (PLA), poly (lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (orthoester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), Solef® PVDF (polyvinylidene fluoride), poly(urea-urethanes), and combinations thereof.

Examples of hydrophilic polymers include, but are not limited to, polymers and co-polymers of hydroxylethyl methacrylate (HEMA), poly(methyl methacrylate) (PMMA), PEG acrylate (PEGA), PEG methacrylate, phosphorylcholine, 2-methacryloyloxyethyl phosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), poly(ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), hydroxy functional poly(vinyl pyrrolidone), polyalkylene oxide, dextran, dextrin, sodium hyaluronate, hyaluronic acid, heparin, elastin, chitosan, and combinations thereof.

Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, polyhydroxyalkanoates (PHAs), poly(ester amides); amino acids; PEG and/or alcohol groups, polycaprolactones, poly(L-lactide), poly(D,L-lactide), poly(D,L-lactide-co-PEG) block copolymers, poly (D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly (amino acids), polycyanoacrylates, poly(trimethylene carbonate), poly(imino carbonate), polycarbonates, polyurethanes, copoly(ether-esters) (e.g., PEO/PLA), polyalkylene oxalates, polyphosphazenes, PHA-PEG, and any derivatives, analogs, homologues, salts, copolymers and combinations thereof.

The stent assemblies of the present invention can comprise an agent. The agent can be included in a stent coating or included in the body of the stent such as, for example, a biodegradable polymeric stent. The agents can be biobeneficial, bioactive, or both biobeneficial and bioactive. An "agent" is a moiety that may be bioactive, biobeneficial, or both bioactive and biobeneficial. A "moiety" includes, but is not limited to, functional groups composed of at least 1 atom, bonded residues in a macromolecule, individual units in a copolymer and entire polymeric blocks.

A "bioactive agent" is a moiety that is mixed, blended, bonded or linked to a polymer coating, or to a polymer from which a stent is made, and provides a therapeutic effect, a prophylactic effect, both a therapeutic and a prophylactic effect, or other biologically active effect upon release from the stent. The bioactive agents of the present invention may remain linked to a portion of the polymer or be released from the polymer. A "biobeneficial agent" is an agent that can be mixed, blended, bonded or linked to a polymer that provides a biological benefit within a mammal without necessarily being released from the stent.

Biobeneficial agents are moieties that may be mixed, blended, bonded or linked to a polymer and are capable of providing a biological benefit such as, for example, control of protein adsorption on an implant surface, without being released from the polymer. Biobeneficial agents can have a reactive group that can be used to link the agent to a polymer. Examples of reactive groups include, but are not limited to, hydroxyl, carboxyl, and amino groups. In some embodiments, the molecular weight of the agent should be at or below about 40,000 Daltons, or any range therein, to ensure elimination of the agent from a mammal. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein.

Examples of biobeneficial agents include, but are not limited to, poly(alkylene glycols), poly(N-vinyl pyrrolidone), poly(acrylamide methyl propane sulfonic acid), poly(styrene sulfonate), sulfonated dextran, polyphosphazenes, poly (orthoesters), poly(tyrosine carbonate), hyaluronic acid, heparin and any derivatives, analogs, homologues, congeners, salts, copolymers and combinations thereof. It is to be appreciated that one skilled in the art should recognize that some of the groups, subgroups, and individual biobeneficial agents may not be used in some embodiments of the present invention.

The poly(alkylene glycols) include, but are not limited to, poly(ethylene glycol) (PEG), methoxy poly(ethylene glycol) (mPEG), poly(ethylene oxide), poly(propylene glycol) (PPG), poly(tetramethylene glycol), poly(ethylene oxide-co-propylene oxide) and any derivatives, analogs, homologues, congeners, salts, copolymers and combinations thereof. In one embodiment, the poly(alkylene glycol) is mPEG.

The copolymers that may be used as biobeneficial agents include, but are not limited to, any derivatives, analogs, homologues, congeners, salts, copolymers and combinations of the foregoing examples of biobeneficial agents. Examples of copolymers that may be used as biobeneficial agents in the present invention include, but are not limited to, copolymers of PEG and hyaluronic acid; copolymers of PEG and heparin; graft copolymers of poly(L-lysine) and PEG; and, any derivative, analog, congener, salt, or combination thereof, of the copolymers. In one embodiment, the copolymer that may be used as a biobeneficial agent is a copolymer of PEG and hyaluronic acid, or any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.). Antineoplastics or antimitotics include, for example, paclitaxel (TAXOL®, Bristol-Myers Squibb Co.), docetaxel (TAXOTERE®, Aventis S. A.), docetaxel, methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

It should be appreciated that the agents of the present invention can have both biobeneficial and bioactive properties, and that classification of an agent as a biobeneficial agent does not preclude the use of that agent as a bioactive agent. Likewise, classification of an agent as a bioactive agent does not preclude the use of that agent as a biobeneficial agent.

A releasable connection 104 used in the present invention can be formed using any process to create a connection between the stent 103 and the balloon 102 that will release upon inflation of the balloon 102 without substantially damaging the stent 103. A stent 103 is "substantially damaged" when the stent 103 can no longer adequately perform its function in a mammal. The term "release" includes, for example, a failure of a connection between the stent 103 and the balloon 102 such that the catheter assembly 100 can be removed from the stent-catheter assembly without either damaging the stent 103 or displacing the stent 103 from its intended position in a mammal.

The term "failure" includes, for example, (i) a loss of a connection within the releasable connection 104; (ii) a loss of a connection between (a) the releasable connection 104 and a material composing the balloon 102 or (b) the releasable connection 104 and a material composing the stent 103; (iii) a loss of a connection between a coating and (a) an underlying material composing the stent 103, (b) an underlying material composing the balloon 102 or (c) the releasable connection 104; and, combinations thereof. The release can occur at any time during expansion of the balloon 102 such as, for example, upon initiation of the expansion, at any time during expansion, or upon completion of the expansion to its intended expanded diameter. In some embodiments, the release can begin at any time during expansion of the balloon 102 and be completed when the balloon 102 is within the range of its intended expanded configurations, such that failure of the releasable connection 104 occurs gradually during expansion.

The strength of the releasable connection 104 and, more importantly, the force required to release the stent 103 from the balloon 102 can be controlled, for example, by (i) selection of the process used to form the releasable connection 104 such as, for example, adhesive bonding, heat staking or welding; (ii) addition of fillers and additives in the materials used to form the releasable connection 104 such as, for example, curing agents; accelerators; antioxidants; impact modifiers; lubricants; glass fillers; PTFE fillers; colorants; antistatics; plasticizers; minerals such as, for example, $CaCO_3$; cellulose; dielectrics; carbon fiber; metal oxides; graphite; and, any other moieties that may be mixed or combined as either in-chain or as pendant functional groups; (iii) selection of a surface treatment method to use prior to formation of the releasable connection 104; (iv) selection of a coating that will serve as a bonding surface such as, for example, a surface on the stent 103 or on the balloon 102 that can serve as a point of failure for the releasable connection 104 to release the stent 103; (v) selection of the size and geometry of a connection to, for example, control the size of the connected area upon which stress is concentrated or to control the stress distribution at the releasable connection 104, both of which may be affected by, for example, the choice of strut dimensions within the stent 103; (vi) selection of materials with different coefficients of expansion to induce stress in the releasable connection 104; and, (vii) combinations thereof.

The term "surface treatment" includes, for example, a variety of chemical, mechanical and combined chemical and mechanical treatments and is discussed below. The term "on" is intended to be defined broadly when used to describe relationships between components such that surface-to-surface contact is not required unless otherwise specified; intermediary elements or materials can be included between the described components.

The releasable connection 104 can be formed using processes that include, but are not limited to, adhesion bonding, heat staking, and welding. One of skill in the art can control each of these processes using any one or combination of the methods described above to form a connection that releases the stent 103 upon inflation of the balloon 102. It should be appreciated that the area covered by the releasable connection 104 can encompass a cumulative area that can be any percentage of the area of contact between the stent 103 and the catheter assembly 100. In some embodiments, the cumulative area covered by the releasable connection 104 can range from about 0.00001% to about 100%, from about 0.0001% to about 90%, from about 0.001% to about 80%, from about 0.01% to about 70%, from about 0.1% to about 65%, from about 1% to about 50%, from about 10% to about 40%, from about 15% to about 35%, from about 20% to about 30%, and any range therein, of a total luminal surface area of the stent 103.

The "total luminal surface area" is the area of the stent 103 facing a lumen within a mammal after delivering the stent 103 to hold open or expand the lumen. In other embodiments, the area covered by the releasable connection 104 can range from about 0.1 nanometer to about 100 micrometers, from about 1 nanometer to about 1 micrometer, from about 10 nanometers to about 100 nanometers, from about 20 nanometers to about 60 nanometers, or any range therein.

It should be appreciated that the area of contact between the stent 103 and the catheter assembly 100 can vary considerably. In some embodiments, the maximum limit to the area of contact can be the total luminal surface area of the stent 103. In other embodiments, the minimum limit to the area of contact can be the minimal amount of adhesive necessary to obtain a releasable connection 104 that is sufficient for delivery of the stent 103 without failure of the releasable connection 104. In other embodiments, only portions of the stent 103 may create the area of contact such as, for example, a case where the total luminal surface area that can contact a catheter assembly 100 is limited to the total luminal surface area of struts in the stent 103.

Figure 2A:
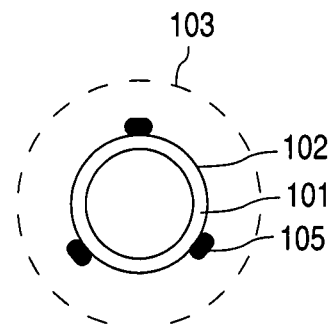
FIGS. 2a and 2b illustrate a method of constructing a medical assembly with a releasable connection formed by adhesion bonding between a stent and a catheter according to embodiments of the present invention.
Figure 2B:
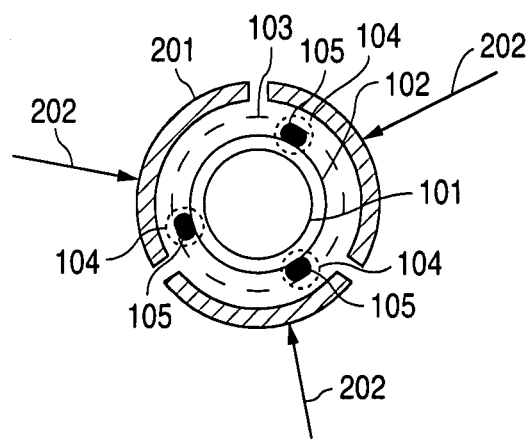

FIGS. 2a and 2b illustrate a method of constructing a medical assembly with a releasable connection formed by adhesion bonding between a stent and a catheter according to embodiments of the present invention. In FIG. 2a, an end-view of the components of a stent-catheter assembly are shown, where the stent 103 is in an expanded state and is placed over the balloon 102 during formation of the stent-catheter assembly. The balloon 102 is in an uninflated state on catheter body 101, and the releasable connection 104 is formed using an adhesive 105 that is placed in predetermined regions on the outer surface of the balloon 102 and/or the inner surface of the stent 103. The predetermined regions encompass a cumulative area that is calculated based on the type of adhesive used, the materials that compose the surface of the stent 103 and the surface of the balloon 102, the use of any surface treatments and the use of any other process variables such as, for example, additives and fillers that may alter the strength of the releasable connection.

In FIG. 2b, pressure 202 is applied to pressurizing structure 201 to reduce the diameter of stent 103, contact the adhesive 105, and form the releasable connection 104 between the stent 103 and the balloon 102. The pressure 202 can be from any source and the pressurizing structure 201 can be made of any materials. In one embodiment, the pressure 202 can be applied radially inward on a pressurizing structure 201 composed of a multitude of solid elements that encircle the stent 103. In another embodiment, the pressure 202 can be applied radially inward on a pressurizing structure 201 composed of a multitude of solid elements that are heated and encircle stent 103. In another embodiment, the pressure 202 can be a pressurized gas or fluid that is applied radially inward on pressurizing structure 201 composed of an elastomeric material that encircles stent 103.

It should be appreciated that the process may be varied in ways known to one of skill in the art. These variations may be introduced, for example, to make the process compatible with other materials. In one example, the pressure 201 can be assisted by the application of heat to assist in reducing the diameter of the stent 103 to form the releasable connection 104. In another example, the adhesive 105 can be placed on predetermined regions of the inner surface of the stent 103 or on predetermined regions of the surface of the balloon 102. In another example, the stent 103 can be formed with a reduced diameter and placed around the balloon 102 to form the releasable connection 104 without applying pressure 201.

The types of adhesives that may be used in the adhesion bonding processes of the present invention include, but are not limited to, adhesives falling into the class of thermosets such as, for example, epoxies, polyesters and phenolics; thermoplastics such as, for example, polyamides, polyesters and ethyl vinyl acetate (EVA) copolymers; and elastomers such as, for example, natural rubber, styrene-isoprene-styrene block copolymers, and polyisobutylene. Other adhesives include, but are not limited to, proteins; cellulose; starch; poly(ethylene glycol) and derivatives and copolymers thereof. In some embodiments, the poly(ethylene glycol) can range in molecular weight from about 500 Daltons to about 50,000 Daltons; from about 500 Daltons to about 40,000 Daltons; from about 500 Daltons to about 30,000 Daltons; from about 500 Daltons to about 20,000 Daltons; from about 600 Daltons to about 10,000 Daltons; from about 750 Daltons to about 7,500 Daltons; from about 800 Daltons to about 5000 Daltons; or any range therein. In other embodiments, the poly(ethylene glycol) has a molecular weight of about 5000 ($PEG_{5000}$). Since PEG is lubricious and water soluble, the application of PEG to a medical assembly can assist in positioning and delivering the medical assembly through a patient's anatomy, and the PEG readily degrades from a medical assembly in vivo.

Mixtures of solvents and another substance can be used to form adhesives. In some embodiments, mixtures of water and sugar such as, for example, mixtures of water and sucrose, can be used as an adhesive. In some embodiments, sucrose is added to water in a concentration (w/w) that ranges from about 50% to about 90%; from about 50% to about 80%; from about 50% to about 70%; from about 55% to about 65%; or any range therein, based on the total weight of the water and the sucrose. In other embodiments, mixtures of PEG, or derivatives thereof, can be mixed with a suitable solvent to form an adhesive. Suitable solvents for PEG, or derivatives thereof, include, but are not limited to, water, ethanol, chloroform, acetone, and the like. In some embodiments, the PEG derivative can be mPEG.

Copolymers may also be used to form adhesives. In some embodiments, copolymers comprising PEG, and derivatives thereof, can be used to form adhesives such as, for example, a triblock copolymer of PLA-PEG-PLA. The triblock copolymers of PLA-PEG-PLA are of a formula

[PLA]-[PEG]-[PLA]

wherein the molecular weight of each PLA block can range from about 500 to about 10,000, from about 500 to about 7,500, from about 500 to about 5000, from about 1000 to about 3000, and any range therein; and, the molecular weight of the PEG can range from about 300 to about 10,000, from about 300 to about 7,500, from about 300 to about 5000, from about 500 to about 2500, and any range therein.

Other classifications of the adhesives that may be used in the adhesion bonding processes of the present invention include, but are not limited to, acrylics such as, for example, light-curing acrylics, cyanoacrylates, anaerobics and modified acrylics; epoxies; polyurethanes; silicones; and pressure-sensitive adhesives. The adhesives may be applied using any method known to one of skill in the art including, but not limited to, dipping, spraying, pouring, brushing, dripping, spin-coating, roller coating, meniscus coating, powder coating, inkjet-type application, or a combination thereof.

In some embodiments, the adhesives may include cyanoacrylates such as, for example, methyl cyanoacrylate, ethyl cyanoacrylate, propyl cyanoacrylate, butyl cyanoacrylate, and methoxyethyl cyanoacrylate. Examples of commercially available cyanoacrylate adhesives include, but are not limited to, Prism® 401 and 4011 (Henkel Loctite Corp.), Super Bonder® 414 (Henkel Loctite Corp.) and Black Max® 380 (Henkel Loctite Corp.). In other embodiments, the adhesives may include light-curing acrylics. Examples of commercially available light-curing acrylics include, but are not limited to, Loctite 3105 and 3311 (Henkel Loctite Corp.). In other embodiments, the adhesives may include two-part, no-mix acrylics. Examples of commercially available two-part, no-mix acrylics include, but are not limited to, Depend® 330 (Henkel Loctite Corp.). In some embodiments, the adhesives can be USP Class I-III or Class V materials. In other embodiments, the adhesives can be USP Class IV or Class VI materials.

In some embodiments, the adhesives can have viscosities ranging from about 1 cP to about 100,000 cP, from about 10 cP to about 50,000 cP, from about 50 cP to about 25,000 cP, from about 100 cP to about 10,000 cP, from about 250 cP to about 1000 cP, and any range therein. Examples of adhesives within these viscosity ranges include, but are not limited to, 300 cP light-curing acrylics, 110 cP ethyl cyanoacrylates, 200 cP rubber-toughened ethyl cyanoacrylates, and 100 cP surface-insensitive ethyl cyanoacrylates.

In some embodiments, certain pressure-sensitive adhesives such as, for example, one listed above, are excluded from the practice of the present invention. In other embodiments, certain thermoplastic adhesives are such as, for example, one listed above, are excluded from the practice of the present invention. In other embodiments, certain thermoplastic adhesives that are tacky at a temperature greater than 37° C. and non-tacky at a temperature greater than 47° C. such as, for example, one listed above, are excluded from the practice of the present invention. In other embodiments, certain photodegradable adhesives such as, for example, one listed above, are excluded from the practice of the present invention.

Heat staking creates a releasable connection that is more of a mechanical connection, whereas adhesion bonding creates releasable connection that is more of a chemical connection. Heat staking forms a molten plastic or polymer into a shape that solidifies to mechanically capture or retain a second component with a first component and, in some embodiments, a second component that is made of a different material than the first component. Heat staking may be used where a releasable connection may be difficult or impossible to form by adhesion bonding. In one embodiment, a stent 103 is connected to an underlying catheter assembly 100 by heat staking a molten plastic connection that is released by breaking the molten plastic connection upon expansion of the balloon 102. Again, as indicated before, the releasable connection 104 can be broken off of the body of a stent, off of a coating on a stent, off of a balloon 102, off of coating on a balloon 102, off of an intermediary material such as a coating, or the releasable connection 104 itself can be broken into pieces.

The welding processes used in the present invention include, but are not limited to, solvent welding, thermal welding, friction welding, and electromagnetic welding. Solvent welding is the softening of the surfaces of two substrates by wetting the substrates with solvents, which may include a polymer or adhesive, and connecting the surfaces chemically or physically to form a fused union. While not intending to be bound by any theory or mechanism of action, a proposed mechanism of solvent welding includes using a solvent to solubilize each material's surface, or an intermediary polymeric or adhesive material, in the area to be connected and create dissolved polymer chains that connect the materials. In this proposed mechanism, dissolved polymer chains mutually invade each material's surface, the solvent absorbs or evaporates, and a dry, solidified connection is formed. Accordingly, the solvents selected for the solvent welding should substantially solubilize the materials to be connected. A material is "substantially soluble" in a solvent when the material can solubilize to an extent great enough to liberate dissolved polymer chains to a degree sufficient to form a connection with an adjoining material.

The solvents used in the present invention should be selected to avoid adversely affecting the medical assembly such as, for example, by solubilizing the stent 103 or the balloon 102 to the extent that it can no longer function as intended. In one example, the balloon 102 is soluble in a highly polar solvent but is reasonably insoluble in a low polarity solvent. A material is "reasonably insoluble" in a solvent when the material does not solubilize to an extent great enough to significantly affect the performance of the resulting product, meaning that the product can still be used for its intended purpose. In this example, the stent 103 is substantially soluble in a low polarity solvent, so the low polarity solvent can be applied to the stent 103 without disrupting the structure of the balloon 102. As in any embodiment of the present invention, embodiments that use solvents can also include an intermediary material such as, for example, a coating that may serve as an interface in the formation of a releasable connection 104 with another surface.

In some embodiments, a coating can be selected to protect an underlying material by choosing a coating that has a lower solubility in a solvent than the underlying material. Such a coating can form the releasable connection 104 with another surface using a solvent that would otherwise solubilize the underlying material to an extent great enough to affect the performance of the resulting product. In other embodiments, a coating can be selected to augment the solubility of an underlying material by choosing a coating that has a higher solubility in a solvent than an underlying material. Such a coating can form the releasable connection 104 with the other surface where the underlying material is not substantially soluble in the solvent. These coatings may also be included to serve as a point of failure for the releasable connection 104 in order to avoid any damage to the stent 103 or the balloon 102.

The solvent may be chosen based on several criteria including, for example, its polarity, molecular size, biocompatibility, reactivity and purity. Other physical characteristics of the solvent may also be taken into account, including the solubility limit of the polymer in the solvent; oxygen and other gases in the solvent; the viscosity and vapor pressure of the combined solvent and polymer; the ability of the solvent to diffuse through an underlying material; and the thermal stability of the solvent. One of skill in the art has access to scientific literature and data regarding the solubility of a wide variety of polymers. Furthermore, one of skill in the art will appreciate that the choice of solvent may begin empirically by calculating the Gibb's free energy of dissolution using available thermodynamic data. Such calculations allow for a preliminary selection of potential solvents to test in a laboratory.

It is recognized that process conditions can affect the chemical structure of the underlying materials and, thus, affect their solubility in a solvent. It is also recognized that the kinetics of dissolution are a factor to consider when selecting a solvent, because a slow dissolution of a material may not affect the performance characteristics of a product where the product is produced relatively quickly.

The solvents can include, but are not limited to, chloroform, DMAC, DMF, THF, cyclohexanone, xylene, toluene, acetone, water, methanol, ethanol, propanol, i-propanol, methyl ethyl ketone, propylene glycol monomethyl ether, methyl butyl ketone, ethyl acetate, n-butyl acetate, dioxane and combinations thereof. Examples of solvent combinations include, but are not limited to, chloroform and acetone (50/50); DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

In some embodiments, the solvents can be polar. In these embodiments, the polar solvents can include acetone, methanol, ethanol, or i-propanol. In other embodiments, the solvents can be non-polar. In these embodiments the solvents can include acetone, chloroform, carbon tetrachloride, tetrachloroethylene, or dichloromethane. In other embodiments, the solvents can be amphiphilic. In other embodiments, the solvents can be an alkyl halide such as, for example, methylene chloride or ethylene dichloride. In other embodiments, the solvents can be rated as Class 3 solvents according to the ICH Guidelines (Guidance for Industry, Q3C Impurities: Residual Solvents, CDER, Rockville, Md. 20857). In other embodiments, the solvents can be rated as Class 2 solvents according to the ICH Guidelines. See Id. In other embodiments, the solvents can be rated as Class 1 solvents according to the ICH Guidelines. See Id.

The adhesives and solvents may be applied using any method known to one of skill in the art including, but not limited to, dipping, spraying, pouring, brushing, dripping, spin-coating, roller coating, meniscus coating, powder coating, inkjet-type application, vapor phase application, or a combination thereof. In some embodiments, adhesives can be activated by the addition of a solvent. In other embodiments, residual solvents can be removed, for example, by allowing the solvent to evaporate under ambient conditions without, or alternatively with, additional application of heat; oven drying; vacuum drying; critical-point drying; convection drying; solvent exchange with a solvent that has a higher vapor pressure; or a combination thereof.

Thermal welding includes, but is not limited to, heated-tool welding, hot-gas welding, extrusion welding, implant-resistance welding and impulse welding. Each of these processes use the application of pressure and an external source of heat to join surfaces. Heated-tool welding applies heat directly by contacting the surfaces to be joined with a heating element. Hot-gas welding uses a focused application of a heated, compressed gas to melt and join surfaces. Extrusion welding melts and injects a material between surfaces to join them. Implant resistance welding and impulse welding are similar in that they both use an imbedded, conductive wire or mesh materials that generate heat when subjected to the resistance of an electric current.

In some embodiments, the process of forming releasable connection 104 includes injecting a melted material between the balloon 102 and the stent 103. In other embodiments, the process of forming releasable connection 104 includes applying a melted material between the balloon 102 and the stent 103 followed by crimping the stent 103 on the balloon 102; on an inner surface of the stent 103 and/or on an outer surface of the balloon 102 prior to placing the stent 103 over the balloon 102; or, on an inner surface of the stent 103 and/or on an outer surface of the balloon 102 prior to crimping the stent 103 on the balloon 102.

Figure 3A:
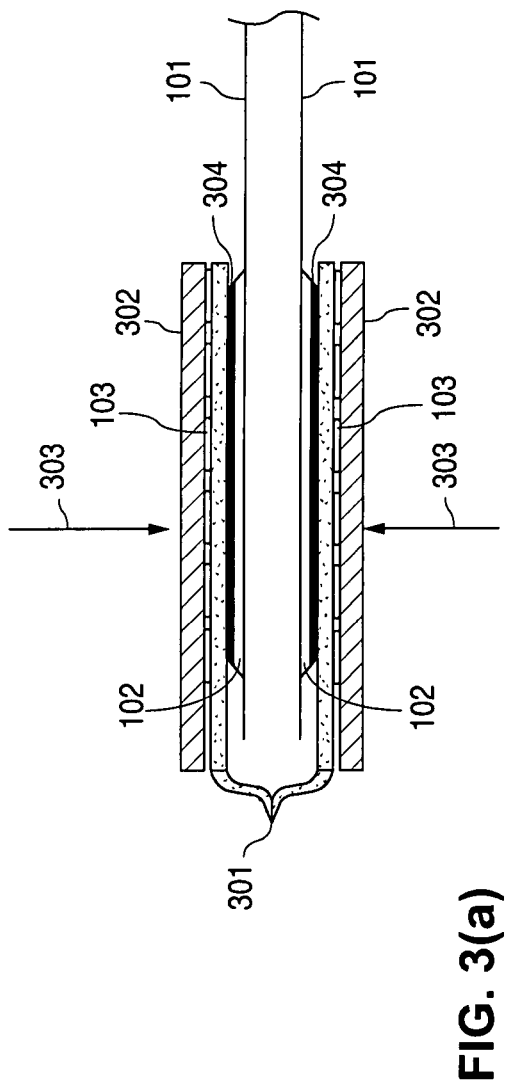
FIGS. 3a and 3b illustrate a method of constructing a medical assembly by heated-tool welding according to embodiments of the present invention.
Figure 3B:
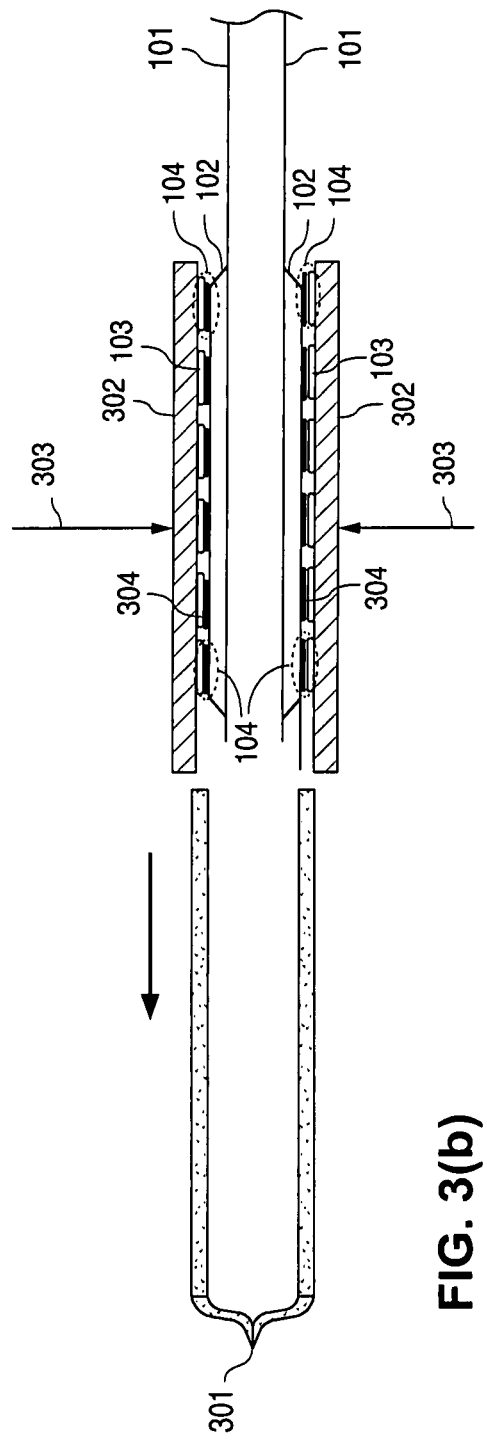

In some embodiments, the heated-tool welding process forms a releasable connection 104 by subjecting the stent 103 and the balloon 102 to pressuring, heating, and joining. FIGS. 3a and 3b illustrate a method of constructing a medical assembly by heated-tool welding according to embodiments of the present invention. In FIG. 3a, the balloon 102 is in an uninflated state on catheter body 101. A heating element 301 is placed between the balloon 102 and the stent 103. A source of pressure 303 is applied to the stent 103 and the balloon 102 using a pressurizing structure 302 that is placed around the stent 103. Heat is then applied to a predetermined region using heating element 301 to form a molten layer 304 on the inner surface of the stent 103, the outer surface of the balloon 102, or both. The predetermined region encompasses a cumulative area that is calculated based on factors such as, for example, the type of adhesive used; the materials that compose the surface of the stent 103 and the surface of the balloon 102; the use of any surface treatments; and, the use of any other process variables such as, for example, additives and fillers that may alter the strength of the releasable connection. In FIG. 3b, the heating element 301 is quickly removed, and the stent 103 and the balloon 102 are joined by applying pressure 303 using a pressurizing structure 302 that is place around the stent 103 to produce the releasable connection 104.

It should be appreciated that in some embodiments, the materials chosen for use with any thermal welding process should be structurally capable of becoming molten in predetermined regions and forming a releasable connection 104 without affecting the function of the medical assembly. As in any embodiment of the present invention, thermal welding processes can include a intermediary material such as, for example, a coating that can serve as an interface in the formation of the releasable connection 104.

In some embodiments, a coating can be selected to protect an underlying material by choosing a coating that has a higher melting point than the underlying material. Such a coating can form the releasable connection 104 with another surface using a temperature that would otherwise melt the underlying material to an extent great enough to affect the performance of the resulting product. In other embodiments, a coating can be selected to augment the underlying material by choosing a coating that has a lower melting point than an underlying material. Such a coating can form the releasable connection 104 with the other surface where the underlying material cannot at a given temperature. These coatings may also be included to serve as a point of failure for the releasable connection 104 in order to avoid any damage to the stent 103 or the balloon 102.

In some embodiments, the process of forming a releasable connection 104 can include applying pressure to the stent 103 during the application of the heat and/or subsequent to the application of heat. In other embodiments, the method of forming a releasable connection 104 additionally comprises crimping the stent 103 on the balloon 102 and heating, wherein the heat is applied (i) prior to crimping the stent 103 on the balloon 102, while crimping the stent 103 on the balloon 102; and/or after crimping the stent 103 on the balloon 102.

Friction welding includes, but is not limited to, ultrasonic welding, vibration welding and spin welding. Each of these processes convert mechanical energy into heat to join surfaces. Ultrasonic welding is focused, fast and efficient, which makes it suitable for joining small components through an internal molecular friction creating a strain amplitude. The "loss modulus" of a plastic determines its ability to develop heat at a specific amplitude, where a higher loss modulus generates more heat at specific amplitude. The major factors that determine the strength of the connection in ultrasonic welding are part and joint design, vibration amplitude, horn selection and fixture design.

Figure 4:
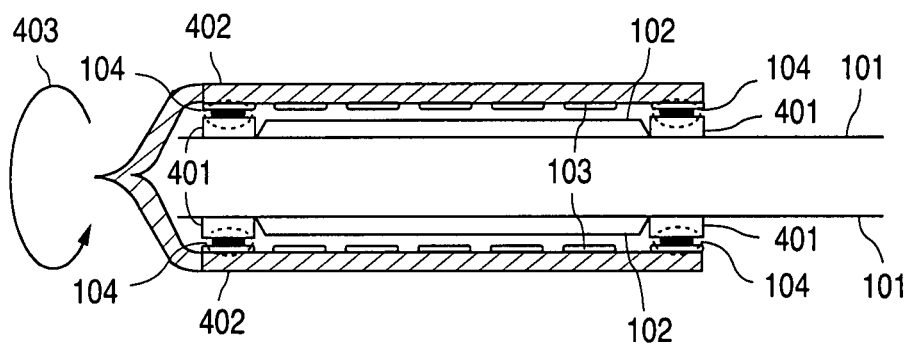
FIG. 4 illustrates a method of constructing a medical assembly by spin welding according to embodiments of the present invention.

Vibration welding is similar to ultrasonic welding in that vibration creates a linear or circular motion to develop the heat to join the surfaces. FIG. 4 illustrates a method of constructing a medical asembly by spin welding according to embodiments of the present invention. In FIG. 4, the balloon 102 is in an uninflated state on the catheter body 101. Stent 103 placed around the balloon 102. In this embodiment, catheter body 101 has a boss 401 at each end of the balloon 102, and the boss 401 serves as a race for the stent 103. A chuck 402 is placed around the stent 103, and a rotating force 403 is applied to the chuck 402 to spin the stent 103 on the boss 401. In this embodiment, heat is generated by the friction created between the stent 103 and the boss 401, and this heat joins the surfaces to create the releasable connection 104.

It should be appreciated that spin welding is a thermal process that can be modified as described above to form a desired releasable connection 104 in a medical assembly. In addition, plastics with a relatively higher coefficient of friction may be better suited for spin welding in some embodiments. Furthermore, it should be appreciated that spin welding may be applicable in any embodiment where any form of a race can be created between the stent 103 and any surface to form the releasable connection 104. As in any embodiment of the present invention, friction welding processes can include a intermediary material such as, for example, a coating that can serve as an interface in the formation of the releasable connection 104 as described above.

In some embodiments, the releasable connection 104 can be formed directly between the stent 103 and the balloon 102 without the use of the boss 401. In other embodiments, the releasable connection 104 can be formed between the stent 103 and the catheter body 101, where the boss 401 is on the inner surface of the stent 103 rather than the catheter body 101. In other embodiments, the releasable connection 104 can be formed between the stent 103 and an intermediary coating, where the coating can be on the surface of the stent 103, the balloon 102, the boss 401, any combination thereof, or on another coating between the stent 103 and the balloon 102. In other embodiments, the releasable connection 104 can be formed between the stent 103 and the catheter body 101 by spinning the stent around the balloon; spinning the balloon within the stent; or spinning both the balloon and the stent to connect the stent to the balloon.

Electromagnetic welding includes, but is not limited to, implant induction welding, radio frequency welding, microwave welding, infrared welding and laser welding. Each of these processes relies on absorption of electromagnetic energy, which is converted into heat to join the surfaces and create the releasable connection 104. As in any embodiment of the present invention, electromagnetic welding processes can include an intermediary material such as, for example, a coating that can serve as an interface in the formation of the releasable connection 104 as described above.

In implant induction welding, a consumable implant is embedded at the interface between the surfaces to be joined and a alternating magnetic field is generated by a coil surrounding the implant. High frequency current (e.g., less than 15 megahertz) is used. If the consumable implant is a conductive implant, the alternating magnetic field produces eddy currents that generate heat to join the surfaces and create the releasable connection 104. If the consumable implant is a ferromagnetic implant, the alternative magnetic field creates hysteresis losses that generate heat to join the surfaces and create the releasable connection 104. As in any embodiment of the present invention, implant induction welding processes can include an intermediary material such as, for example, a coating that can serve as an interface in the formation of the releasable connection 104 as described above.

In radiofrequency welding, polar molecule rotation is induced in a rapidly changing electric field and, as such, radiofrequency welding is a good process for polar materials such as polyvinylchloride, nylon and EVA. The FCC restricts this process to operate at specific frequencies that are multiples of 13.56 megahertz, and most radiofrequency welding processes operate at 27.12 megahertz. Small bond lines are a major benefit of this welding process, which is useful in forming releasable connection 104. Microwave welding is very similar to radiofrequency welding and operates at a higher frequency of about 2450 megahertz. Non-polar materials can be welded by inserting an "absorber," which may be a polar material, at the joint interface to generate the heat. As in any embodiment of the present invention, radiofrequency welding processes can include a intermediary material such as, for example, a coating that can serve as an interface in the formation of the releasable connection 104 as described above.

Infrared welding and laser welding are state-of-the-art techniques that are well-suited for "through-transmission" welding. Through-transmission welding passes energy through a non-absorbing layer into an absorbing layer that generates heat to join the surfaces and create the releasable connection 104. In infrared welding, a broadband infrared source is used to generate the heat, and the absorption and thermal conductivity of the plastic are variables to consider in designing the process. In one embodiment, additives that include, but are not limited to, carbon-black and various inorganics can be used to increase absorption of infrared energy and control heating. Good sources of broadband infrared energy include, but are not limited to, tungsten lamps, ceramic heaters, halogen lamps, and radiant tubular heaters. As in any embodiment of the present invention, infrared welding processes can include an intermediary material such as, for example, a coating that can serve as an interface in the formation of the releasable connection 104 as described above.

In laser welding, $CO_2$, Nd:YAG, and diode lasers are used to generate the heat, and the choice of laser affects the depth of operation. For example, $CO_2$ lasers operate at about 10.6 microns, which falls into the C—C absorption band, and are limited to depths of about 0.5 mm in plastics, which limits $CO_2$ laser welding to applications where the parts to be connected are thin. Since the Nd:YAG laser operates at about 1.06 microns, it is suitable for through-transmission welding since most polymers will not absorb Nd:YAG laser energy. The Nd:YAG laser welding process is particular suitable for small and delicate parts, since the parts can be pre-assembled and vibration is not required. In one embodiment, fiber optics, focusing lenses and mirrors can be used to deliver, direct and focus laser energy to predetermined regions to control the strength of the releasable connection 104. In another embodiment, fillers and additives such as, for example, glass fibers, impact modifiers and flame-retardants, can be added to the materials to further control the welding by dispersing the energy. As in any embodiment of the present invention, laser welding processes can include a intermediary material such as, for example, a coating that can serve as an interface in the formation of the releasable connection 104 as described above.

The diode laser welding process is similar in operation to the Nd:YAG laser welding process and can be designed to operate at a variety of wavelengths, depending on the element used to construct the laser diode. A common laser diode operates at 0.81 microns and generates about 50 watts of power. In one embodiment, multiple diodes at a variety of wavelengths can be arranged to provide a variety of welding configurations and sufficient welding power. In another embodiment, fiber optics are used.

The releasable connections 104 may be cured, which can occur in the presence or absence of oxygen at room temperature, or with the application of energy such as, for example, heat, electromagnetic radiation, electron beam, ion or charged particle beam, neutral-atom beam energy, or a combination thereof. The energy can be applied locally, focused to the point of the connection; or, to an entire assembly to cure an adhesive. Methods of heating can include, but are not limited to, convention or conduction ovens, hot plates, microwave heating, infrared heating, vapor-phase heating, liquid-phase heating, laser heating, and combinations thereof. Electromagnetic radiation may include light and can be applied as a broadband energy or in specific wavelengths.

In some embodiments, the energy can be electromagnetic radiation in the wavelength range of from about 150 nm to about 600 nm. In other embodiments, the energy can be ultraviolet light is in the wavelength range of from about 157 nm to about 436 nm. In other embodiments, the energy can be ultraviolet light is in the wavelength range of from about 300 nm to about 400 nm. In other embodiments, the energy can be laser energy from a Nd:YAG or $CO_2$ laser. In other embodiments, the energy is variable-frequency microwave energy. Curing agents may also be used. In some embodiments, the curing agents include, but are not limited to aromatic amines, anhydrides, carboxylic acids, phenol novolacs, amino resins, isocyanates, diisocyanates, and combinations thereof. In other embodiments, copolymerizing agents such as cyclohexanedimethanol and isophthalic acid can be used.

Surface treatment can be used to control the strength and durability of a connection and, thus, to control the onset of connection failure in any of the embodiments of the present invention. Surface treatments are generally mechanical, chemical, or a combination of mechanical and chemical treatments. Mechanical surface treatment includes, but is not limited to, surface roughening through abrading; blasting with grit, shot, or laser energy; and, abrading a surface in the presence of an adhesive. Chemical surface treatment includes, but is not limited to, degreasing; etching such as, for example, chromic acid etching; iodine treatment; sodium treatment; surface grafting; anodizing; adding adhesion promoters such as, for example, primers including, but not limited to silane- and isocyanate-based primers; promoting transcrystalline growth; thermal, flame, UV, corona discharge and plasma treatments; and, addition of a polymeric layer that will release from an underlying layer upon expansion of a balloon 102.

It is to be appreciated that surface treatments can be used to control the release of a connection between a stent 103 and a balloon 102. For example, one of skill in the art can use surface treatments to control (i) the number of reactive sites or wettability of a surface by, for example, using techniques such as corona discharge, flame treatment, UV exposure, thermal treatment, and plasma treatment to introduce reactive moieties on a surface such as, for example, hydroxyl, carbonyl, carboxyl, and sulfoxyl, aldehyde, hydroperoxide, ether, ester, amino and amido groups; (ii) the number of unsaturated bonds on a substrate surface; (iii) the number of sites available for mechanical interlocking between polymers and a substrate surface; (iv) the crystallinity of a surface such as, for example, by using an iodine treatment to convert a surface that has an alpha form to a surface that has a beta form, by using a sodium treatment to dissolve amorphous regions on a surface, or by using thermal treatment to break and shorten polymeric chains; and, (v) the crosslinking within a substrate surface such as, for example, by using plasma treatment to increase crosslinking within a surface to enhance the strength and wettability of the surface.

Figure 5:
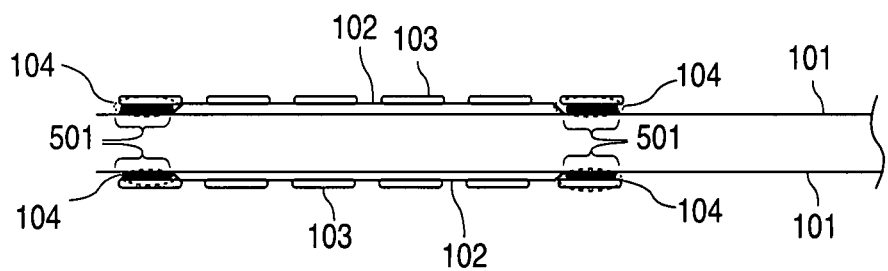
FIG. 5 illustrates a method of constructing a medical assembly with a releasable connection formed between a stent and a catheter body according to embodiments of the present invention.

FIG. 5 illustrates a method of constructing a medical assembly with a releasable connection formed between a stent and a catheter body according to embodiments of the present invention. The medical assembly has a catheter body 101, a balloon 102, a stent 103, and a releasable connection 104. The stent 103 is placed around the balloon 102 and a releasable connection 104 is formed between the catheter body 102 and the stent 103 to complete construction of the medical assembly. In this embodiment, the releasable connection 104 is formed only between the stent 103 and the catheter body 101 in a region 501 that is outside of the region of the balloon 102, such that there is no connection 104 between the balloon 102 and the stent 103. The releasable connection 104 can be formed in the region 501 using any of the methods described above. The balloon 102 can have a deflated configuration and is capable of being enlarged to an expanded configuration. The releasable connection 104 releases the stent 103 from the catheter body 101 in response to enlargement of the balloon 102 or when the balloon 102 has been enlarged to an expanded configuration.

In some embodiments, the stent is a biodegradable stent. In other embodiments, the assembly includes an intermediary material such as, for example, a coating between the releasable connection and the stent. In one embodiment, the releasable connection 104 releases off of the stent. In another embodiment, the releasable connection releases off of the catheter body 101. In another embodiment, the releasable connection 104 releases off of an intermediary material such as, for example, a coating. In another embodiment, the releasable connection 104 releases by breaking apart along a part of the releasable connection 104.

Figure 6A:
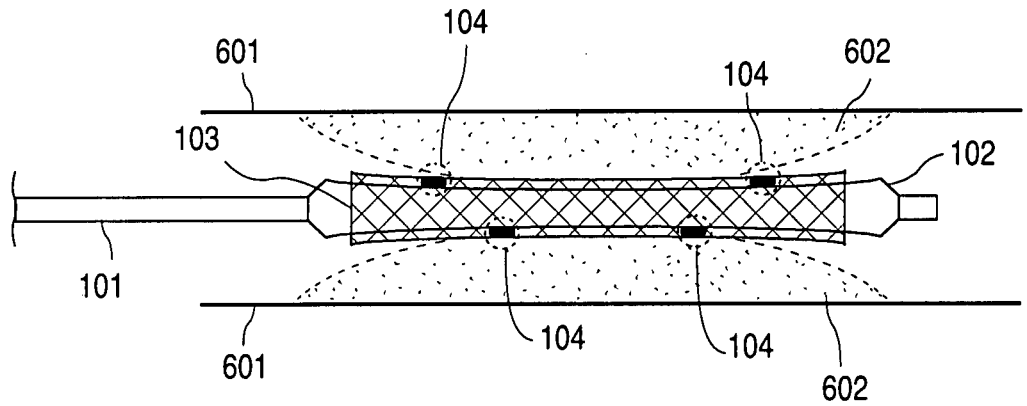
FIGS. 6a-6c illustrate a method for delivering a stent according to embodiments of the present invention.
Figure 6B:
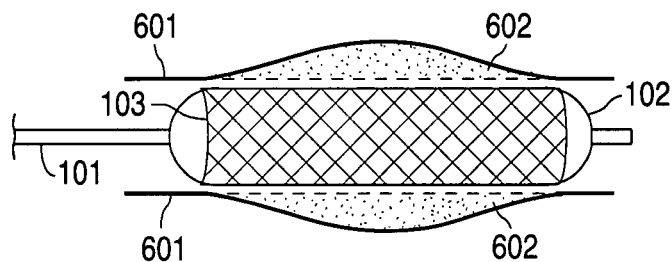
Figure 6C:
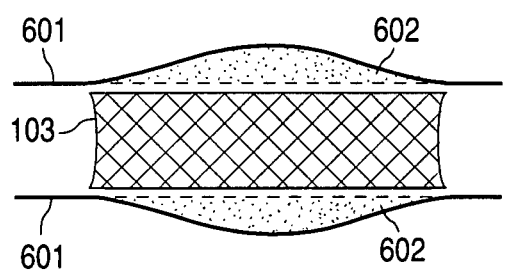

FIGS. 6a-6c illustrate a method for delivering a stent according to embodiments of the present invention. In FIG. 6a, a medical assembly having a catheter body 101, a balloon 102, a stent 103 and an adhesive 104 is positioned in a vascular organ 601 in a region of a vascular lesion 602. The vascular organ 601 has a lumen that is constricted by the presence of a vascular lesion 602. In FIG. 3b, the balloon 102 is inflated to compress against the vascular lesion 602 to remodel the vascular organ 601 and increase the diameter of the lumen of vascular organ 601. As the balloon 102 is inflated, the stent 103 is released from the balloon 102. In FIG. 3c, the balloon 102 has been deflated and withdrawn from the vascular organ 601 to complete delivery of the stent in the region of the vascular lesion 602.

It should be appreciated that the method of delivering a stent can be used in any organ within a mammal within which a stent may provide a benefit. In one embodiment, the method of delivering a stent can be used to deliver a stent in vascular organs such as, for example, coronary arteries or hepatic veins. In another embodiment, the method of delivering a stent can be used to deliver a stent in renal organs such as, for example, urethras and ureters. In another embodiment, the method of delivering a stent can be used to deliver a stent in biliary organs such as, for example, biliary ducts. In another embodiment, the method of delivering a stent can be used to deliver a stent in pulmonary organs such as, for example, tracheas, bronchi and bronchioles. In another embodiment, the method of delivering a stent can be used to deliver a stent in gastrointestinal organs such as, for example, esophagi and colons.

Example 1

A relative comparison of the strengths of the releasable connection 104 can assist in the design of a medical assembly. The relative strengths of the releasable connection 104 can be tested using lap-shear test method ASTM D 1002 or block-shear test method ASTM D 4501. Shear stress may be a good simulation of the stress applied to the releasable connection 104 upon expansion of balloon 102. Lap-shear testing includes substrate failure and other factors such as the modulus of the plastics, which makes it difficult to compare differences due to adhesion bonding. Block-shear testing places a load on a thicker section of a material, which allows a material to withstand a higher load before substrate failure. An Instron 4204 mechanical properties tester, for example, can be used with a load cell that has about a 50 kN capacity at a pull speed of about 0.05 inches/minute in order to test a wide variety of releasable connections that may be used to form medical assemblies of the present invention. This testing method is not intended to be limiting. Other such testing methods known to one of skill in the art may be used in order to identify the proper releasable connection for an intended purpose.

Example 2

Solvent welding was used to form a releasable connection 104 between a polymeric stent 103 and a balloon 102 in the construction of a stent-catheter assembly. A few drops of chloroform were placed on the inner surface of a stent comprising poly(L-lactide). Pressure was applied to the outer surface of the stent to reduce the diameter of the stent and contact the outer surface of the balloon to form a releasable connection using a sliding-wedge, servo crimper. The stent-catheter assembly was vacuum dried to remove any residual chloroform to form the releasable connection.

Example 3

Adhesion bonding was used to form a releasable connection 104 between a polymeric stent 103 and a balloon 102 in the construction of a stent-catheter assembly. An adhesive was made from by mixing sucrose with water, wherein the sucrose was added at a concentration of 70% (w/w) based on the total weight of the sucrose and water.

A first stent-catheter assembly was constructed by applying pressure to the outer surface of the stent with a sliding-wedge, servo crimper to reduce the diameter of the stent until the inner surface of the stent contacted the outer surface of the catheter assembly. The stent-catheter assembly was then coated with the sucrose and water mixture as an adhesive to form the releasable connection.

A second stent-catheter assembly was constructed by coating the contact area between the catheter assembly and the stent with the adhesive. Pressure was then applied to the outer surface of the stent with a sliding-wedge, servo crimper to reduce the diameter of the stent until the inner surface of the stent contacted the outer surface of the catheter assembly that was coated with the mixture of sucrose and water as an adhesive to form the releasable connection.

Example 4

Adhesion bonding was used to form a releasable connection 104 between a polymeric stent 103 and a balloon 102 in the construction of a stent-catheter assembly. A waxy form of poly(ethylene glycol) known as $PEG_{5000}$ was used as the adhesive and was (i) heated and applied as a molten form, (ii) dissolved in water, (iii) dissolved in ethanol, and (iv) dissolved in acetone to form stent-catheter assemblies with releasable connections.

A first stent-catheter assembly was constructed by applying pressure to the outer surface of the stent with a sliding-wedge, servo crimper to reduce the diameter of the stent until the inner surface of the stent contacted the outer surface of the catheter assembly. The stent-catheter assembly was then coated with the molten $PEG_{5000}$ as an adhesive to form a releasable connection. This procedure was also used to form releasable connections in other stent-catheter assemblies using a $PEG_{5000}$ that was dissolved in water, dissolved in ethanol, or dissolved in acetone to form stent-catheter assemblies with releasable connections.

A second stent-catheter assembly was constructed by coating the contact area between the catheter assembly and the stent with the molten $PEG_{5000}$. Pressure was then applied to the outer surface of the stent with a sliding-wedge, servo crimper to reduce the diameter of the stent until the inner surface of the stent contacted the outer surface of the catheter assembly that was coated with the molten $PEG_{5000}$ as an adhesive to form a releasable connection. As in the first catheter assembly, this procedure was also used to form releasable connections in other stent-catheter assemblies using a $PEG_{5000}$ that was dissolved in water, dissolved in ethanol, or dissolved in acetone to form stent-catheter assemblies with releasable connections.

Since $PEG_{5000}$ is lubricious and water soluble, the application of $PEG_{5000}$ to the stent-catheter assembly assists in positioning and delivering the assembly through a patient's anatomy, where the $PEG_{5000}$ readily degrades in vivo.

Example 5

Adhesion bonding was used to form a releasable connection 104 between a polymeric stent 103 and a balloon 102 in the construction of a stent-catheter assembly. A triblock copolymer of PLA-PEG-PLA was used as the adhesive to form stent-catheter assemblies with releasable connections. Each PLA block in the triblock copolymer had a molecular weight of about 500, and the PEG had a molecular weight of about 1000.

A first stent-catheter assembly was constructed by applying pressure to the outer surface of the stent with a sliding-wedge, servo crimper to reduce the diameter of the stent until the inner surface of the stent contacted the outer surface of the catheter assembly. The stent-catheter assembly was then coated with the PLA-PEG-PLA copolymer as an adhesive to form the releasable connection.

A second stent-catheter assembly was constructed by coating the contact area between the catheter assembly and the stent with the PLA-PEG-PLA copolymer. Pressure was then applied to the outer surface of the stent with a sliding-wedge, servo crimper to reduce the diameter of the stent until the inner surface of the stent contacted the outer surface of the catheter assembly that was coated with the PLA-PEG-PLA copolymer as an adhesive to form the releasable connection.

While particular embodiments of the present invention have been shown and described, it will be obvious to those skilled in the art that changes and modifications can be made without departing from this invention in its broader aspects. For example, the teachings of the present invention provide a multitude of ways in which a releasable connection can be formed in a medical assembly and, in particular, a stent-catheter assembly. One of skill in the art will appreciate that the any of the teachings can be used together or in combination to fulfill the purpose and nature of the invention.

We claim:

1. A medical assembly comprising:
a nonbiodegradable stent;
a catheter comprising an expandable member having the stent positioned on the expandable member, the member capable of being expanded from a collapsed profile to an expanded profile; and
an apparatus for releasably connecting the stent to the member such that in response to the expansion of the member, the nonbiodegradable stent is detached from the member, wherein the apparatus comprises:
a cylindrical heating element that is placed between the stent and the expandable member when the stent is disposed around the expandable member, wherein the heating element applies heat to the stent and/or expandable member, wherein the cylindrical heating element is removable to allow releasably connecting the stent to the expandable member,
a pressurizing structure that is placed around the stent disposed around the expandable member to apply inward radial pressure to the stent in conjunction with heat from the heating element to releasably connect the stent to the expandable member.

2. A medical assembly comprising:
a nonbiodegradable stent;
a catheter assembly comprising a catheter body and a balloon having the stent positioned on the balloon, the balloon having a deflated configuration and capable of being enlarged to an expanded configuration; and
a releasable connection between the stent and the catheter body, wherein the releasable connection retains the stent on the catheter body, wherein the releasable connection is formed in a region of the catheter body axially distal or proximal to the balloon, and the releasable connection releases the stent from the catheter body in response to enlargement of the balloon or when the balloon has been enlarged to an expanded configuration, wherein the releasable connection is located between an inner surface of the stent and an outer surface of the catheter body.

3. The assembly of claim 2, wherein the releasable connection releases off of the stent.

4. The assembly of claim 2, wherein the releasable connection releases off of the catheter.

5. The assembly of claim 2, further comprising an intermediary material between the releasable connection and the stent, the releasable connection and the catheter body, or the combination thereof.

6. The assembly of claim 5, wherein the intermediary material is a coating.

7. The assembly of claim 5, wherein the releasable connection releases off of the intermediary material.

8. A method for constructing a medical assembly comprising:
placing a nonbiodegradable stent over a balloon of a catheter assembly; and
forming a releasable connection between the stent and the catheter assembly such that in response to the enlargement of the balloon or when the balloon has been enlarged to an expanded configuration, the stent is detached from the catheter assembly, wherein the forming a releasable connection comprises:
depositing an adhesive material on the catheter assembly and/or an inner side of the stent, the adhesive material being of the type that allows for the detachment of the stent from the catheter assembly in response to the enlargement of the balloon or when the balloon has been enlarged to an expanded configuration;

applying pressure to the stent to allow the adhesive material to contact the stent and catheter assembly to form the releasable connection; and applying heat to assist the pressure to form the releasable connection formed by the adhesive material.

9. The method of claim 8, wherein the balloon is in a collapsed configuration when the releasable connection is formed between the stent and the catheter assembly.

10. The method of claim 8, wherein the releasable connection disengages from the stent.

11. The method of claim 8, wherein the releasable connection disengages from the balloon.

12. The method of claim 8, wherein the releasable connection disengages from the catheter assembly in a region outside of the balloon.

13. The method of claim 8, wherein the releasable connection is configured to break in parts to disengage the stent from the balloon.

14. A method for constructing a medical assembly comprising:

placing a nonbiodegradable stent over a balloon of a catheter assembly; and forming a releasable connection between the stent and the catheter assembly such that in response to the enlargement of the balloon or when the balloon has been enlarged to an expanded configuration, the stent is detached from the catheter assembly, wherein the method of forming the releasable connection comprises:

applying a solvent to an inner surface of the stent and/or an outer surface of the catheter assembly prior to placing the stent over the balloon wherein the stent has a reduced diameter prior to placing the stent over the balloon, the reduced diameter is a diameter for purposes of properly delivering the stent in a lumen within a mammal followed by removing the solvent, wherein the releasable connection is formed by solvent welding to form a fused union.

15. The method of claim 14, wherein the stent includes a material on an inner surface thereof and/or the catheter assembly includes a material on the outer surface thereof, and wherein the solvent is applied to the material on the stent and/or the material on the catheter assembly.

16. The method of claim 15, wherein the releasable connection disengages from the material on the stent, the material on the balloon, the material on the catheter assembly in a region outside of the balloon, or a combination thereof.

17. The method of claim 14, wherein the stent includes a material on an inner surface thereof and/or the catheter assembly includes a material on the outer surface thereof, and wherein the solvent is applied to the material on the stent and/or the material on the catheter assembly.

18. The method of claim 17, wherein the releasable connection disengages from the material on the stent, the material on the balloon, the material on the catheter assembly in a region outside of the balloon, or a combination thereof.

19. A method for constructing a medical assembly comprising:

placing a nonbiodegradable stent over a balloon of a catheter assembly; and forming a releasable connection between the stent and the catheter assembly such that in response to the enlargement of the balloon or when the balloon has been enlarged to an expanded configuration, the stent is detached from the catheter assembly, wherein the forming the releasable connection comprises:

injecting a melted material between the catheter assembly and the stent.

20. A method for constructing a medical assembly comprising:

placing a nonbiodegradable stent over a balloon of a catheter assembly; and forming a releasable connection between the stent and the catheter assembly such that in response to the enlargement of the balloon or when the balloon has been enlarged to an expanded configuration, the stent is detached from the catheter assembly, wherein the forming the releasable connection comprises:

placing a heating element between the stent and the catheter assembly;

applying heat to connect the stent to the catheter assembly.

21. The method of claim 20, wherein the stent is made completely or in-part from a polymeric material.

22. The method of claim 20, wherein the stent includes a material deposited on an inner surface thereof and/or the catheter assembly includes a material deposited on an outer surface thereof, such that application of heat to the material on the stent and/or the material on the catheter assembly allows for connection of the stent to the catheter assembly.

23. The method of claim 22, wherein the material on the stent and/or the catheter assembly has a lower melting temperature than the stent and the catheter assembly.

24. The method of claim 22, wherein the material on the stent and/or the catheter assembly has a higher melting temperature than the stent and the assembly.

* * * * *